United States Patent [19]

Franco

[11] 4,296,100
[45] Oct. 20, 1981

[54] METHOD OF TREATING THE HEART FOR MYOCARDIAL INFARCTION

[76] Inventor: Wayne P. Franco, 79 Two Stone Dr., Wethersfield, Conn. 06109

[21] Appl. No.: 164,074

[22] Filed: Jun. 30, 1980

[51] Int. Cl.$^3$ ............................................. A61K 35/55
[52] U.S. Cl. .................................................. 424/108
[58] Field of Search ......................................... 424/108

[56] References Cited

PUBLICATIONS

Spross et al.–Chem. Abst. vol. 62 (1965), p. 15996e.
Gospodarowicz et al.–Chem. Abst. vol. 86 (1977), p. 40942r.

*Primary Examiner*—Sam Rosen
*Attorney, Agent, or Firm*—Wolf, Greenfield & Sacks

[57] ABSTRACT

The heart is treated with fibroblast growth factor to alleviate conditions caused by myocardial infarctions as by reducing the size of damaged heart areas. An effective dose of fibroblast growth factor when applied to the heart is found to increase blood flow in affected areas for a period of at least 4 hours and often more.

13 Claims, No Drawings

METHOD OF TREATING THE HEART FOR MYOCARDIAL INFARCTION

BACKGROUND OF THE INVENTION

Limitation of the quantity of myocardium damage due to ischemic disease is important in caring for patients with coronary artery disease not only for lowering the immediate mortality rate but also for leaving those who have suffered coronary occlusions with a greater quantity of viable myocardium. There has been experimentation with therapeutic agents aimed at achieving this goal. Nitroglycerin, hyaluronidase, corticosteroids, heparin, mannitol and others have been used in certain areas of the heart after myocardial infarction. Such drugs have not been found to be complete cures for the problems encountered. The drugs have different mechanisms of action which include decreasing myocardial oxygen requirements to maintain viability, increasing myocardial oxygen supply, augmented anaerobic metabolism and protection against autolytic and heterolytic processes.

Fibroblast growth factor (FGF) was first isolated and purified from bovine pituitary glands by Gospodarowicz, D., 1975, *J. Biol. Chem*, Vol. 250, No. 7, 2515–2520 and *Nature*, Vol. 249, May 10, 1974, 123–127. It has in the past been used as a mitogenic agent for a variety of mesodermal cells in vitro. It has been experimented with to increase vascularization in the cornea of laboratory animals. Its use has not in the past been suggested for reducing the cross-sectional infarct size in myocardial infarct cases.

SUMMARY OF THE INVENTION

It is an object of this invention to provide a means and method for use in myocardial infarct, and heart surgery procedures such as coronary bypass operations to reduce the quantity of myocardium damage due to ischemic disease.

It is still another object of this invention to provide a material suitable for use in a method of treating the heart in vivo to increase blood flow for sustained periods of time after myocardial infarction.

According to the invention an area of the heart subject to ischemic disease is treated in vivo to maintain viability of that area for a sustained period of time to salvage the area. An effective dose of FGF is applied to the heart. Preferably the FGF is applied to the heart after myocardial infarction although it can be applied when there is an indication of an impending myocardial infarction. In many cases blood flow is increased in the area treated and surrounding areas. Preferably a slow release medium is used for carrying the FGF as when it is injected directly into the heart. Sephadex gel in a normal saline suspension can be used to carry FGF.

Preferably a dosage of about 10 micrograms to 1 gram of FGF per 100 grams of heart is used directly injected into the heart. When intravenus injection is used, the dosage is preferably high as for example to one milligram while subcutaneous, oral ingestion or other methods are used, the dosage can vary greatly and can be at the high end of the range. At least 10 micrograms/100 grams heart is used to achieve the effect desired. The top end of the range can be any amount that does not have deleterious effects on the body while still giving the desired effect.

The damaged myocardium area is smaller after myocardial infarction when the treatment of this invention is used than if not used. In addition, blood flow as measured in areas damaged by the myocardial infarction and areas therearound can be greatly increased even many hours later.

DESCRIPTION OF PREFERRED EMBODIMENTS

The fibroblast growth factor (FGF) useful in this invention can be obtained from bovine pituitary glands by the method of Gospodarowicz, D., 1975, *J. Biol. Chem.*, Vol. 250, No. 7, 2515–2520 and *Nature*, Vol. 249, May 10, 1974, 123–127, or from other sources such as brain tissue, D. Gospodarowicz, U. Bialecki, G. Greenburg, 1978, *J. Biol. Chem.*, Vol. 253, pps. 3736–3743. The product is available from Collaborative Research, Inc. of Waltham, Massachusetts. The preparation involves acid and ammonium sulfate precipitation followed by dialysis, ion exchange chromatography and gel exclusion chromatography. An additional ion exchange step can be used. The product is a water soluble lyophilized preparation normally supplied in 10 microgram quantities. It is stable at room temperature but preferably stored at $-20°$ reconstitution in normal saline.

Bovine FGF possesses a molecular weight of about 13,400 with an isoelectric point of 9.5. The isoelectric point is confirmed by binding experiments to carboxymethyl Sephadex, a product of Pharmacia Incorporated of Piscataway, New Jersey. Biological assay using BALB/c 3T3 cells or bovine heart endothelial cells demonstrates that the FGF is biologically active in the 1 to 10 nanogram range or 25 to 200 nanogram range respectively. FGF which stimulates BALB/c 3T3 cells and has a mitogenic effect on mammalian endothelial cells with the advantageous effect of this invention can also be obtained from other mammals such as humans.

FGF has a growth promoting effect in various areas as was first described for such pituitary derived proteins by Holley and Kiernan (Holley, R. W. and Kiernan, J. A., 1968, *Proc. Natl. Acad. Sci. USA*, Vol. 60, 300).

The FGF derived from bovine pituitary glands is at least 90% pure. The FGF can be derived from other sources so long as it has the known activities of FGF and acts in accordance with the purposes of the present invention.

Generally, the FGF is preferably used by injecting into the heart in vivo after myocardial infarction in amounts of 10 micrograms to 1 gram per 100 grams of heart. Preferably a series of spaced injections are used to distribute the desired amount of FGF over the area of the heart to be treated. Preferably the FGF is carried in a 2.5% Sephadex G200 normal saline suspension. The carrier for the FGF can vary greatly. In some cases, it is merely suspended in water or saline. However, it is preferred to use some physiologically compatible slow release mechanism such as dextran beads. Macroaggregates of albumin can also be used as an FGF carrier.

The FGF can be used in varying ways to treat any mammal to reduce damaged areas of the heart associated with myocardial infarction. Mammalian hearts to be treated include dog, cat, humans, cow and other animals. Direct injection into the heart tissue or intravenous injection is preferred but subcutaneous, intramuscular and oral ingestion may be used as known from medications of this type. Direct injection can be carried out through the chest or body or into the exposed heart during open heart surgery. Of course amounts must be raised considerably in order to obtain sufficient dosages to affect the heart muscle when other than myocardial injection or intravenous are used.

Specific examples of the present invention are illustrated in the following Examples which are not to be taken as limiting:

EXAMPLE I

A 5% solution of Sephadex G200 (dextran beads produced by Pharmacia Incorporated of Piscataway, N.J.) in sterile normal saline was prepared and allowed to sit for 24 hours. The suspension was then diluted with equal parts of sterile normal saline and served as the control Sephadex suspension. 0.1 ml of 2.5% Sephadex normal saline solution was injected into a vial containing 10 micrograms of Bovine FGF obtained from Collaborative Research, Inc. of Waltham, Mass. The vial was shaken carefully to mix the contents and allowed to sit for 8 hours so that the FGF was absorbed into the Sephadex beads.

Twelve cats weighing approximately 2.5–3.0 kg each were utilized. Infarcts were induced in all twelve cats. The chests were opened with incisions made approximately 3 centimeters above the point of maximum impulse. The ribs were retracted and the pericardium exposed. The pericardium was then opened and the left anterior descending coronary artery (LAD) was exposed. A proximal diagonal branch of the LAD was ligated with 3-0 silk and the heart was covered with sterile normal saline soaked gauze. After a period of 2 minutes, 6 of the 12 animals received an injection of 0.1 ml of control suspension, the other half received 0.1 ml of experimental Sephadex suspension containing FGF. Sephadex is a trademarked product containing dextran beads sold by Pharmacia Fine Products Co. of Piscataway, N.J. The suspensions were injected intramyocardially, one-half of it approximately 3 mm down and 1 mm to the right and the other half 3 mm down and 1 mm to the left of the ligation site.

The FGF material injected contained 10 micrograms of FGF and 100 micrograms of albumin as a carrier and stabilizer.

All the animals were closed and allowed to recover, receiving 800,000 units gentamycin daily through the first 2 post-operative days. After 10 days, all the animals were sacrificed. The hearts were excised and placed in 10% buffered formulin. The left ventricles were sectioned into slices and an attempt was made to find the most damaged area in each heart in which the control group was closely visible yet in the experimental group it was necessary to examine the stain sections under light microscope to demonstrate significant damage. The section that represented the most damaged area of each heart was then projected onto a screen and the cross-sectional area of the entire left ventricle in the infarct portion was measured. The extent of myocardial ischemic injury was estimated by the ratio of cross-sectional area of infarct size to the total cross-sectional area of left ventricle size. In addition the stain sections were examined under light microscope to detect essential differences between control and experimental myocardial conditions.

When all the hearts were initially sectioned, a striking difference between experimental and control hearts was noted. It appeared on gross examination that distal to the ligation site none of the experimental hearts were significantly damaged. However, in all of the control hearts there was gross evidence of infarction. The results of the histologic measurement of infarct size for all animals are shown in Tables I and II. There was an approximate four-fold reduction in infarct size of treated groups versus control groups. This holds true whether Sephadex QAE (a charged Dextran bead) or Sephadex G200 is used and also whether 25 micrograms or 10 micrograms of FGF are used. The only essential difference which contributes to the limitation of infarct size appears to be the addition of FGF to the Sephadex beads.

The above Example I indicates that FGF may play a beneficial role in limitation of infarct size in cat myocardium. Histological study did not show any significant increase in capillaries in the hearts produced by FGF but the ischemic damage of those animals treated with FGF were significantly less than those treated with a control and no FGF. Other dextran beads can be used as a carrier. Alternately in some cases no beads are used and FGF used alone or tagged to albumin or other carrier can be used.

TABLE I

| CONTROL GROUP | | | TREATED GROUP | | |
|---|---|---|---|---|---|
| Animal No. | % Infarct* | Distance from+ Aortic Root | Animal No. | % Infarct* | Distance from+ Aortic Root |
| 1 | 18.7% | 2.6 cm | 7 | 5.6%‡ | 2.8 cm |
| 2 | 13.7%‡ | 2.5 cm | 8 | 4.8%§ | 2.7 cm |
| 3 | 10.6% | 2.6 cm | 9 | 3.5% | 2.5 cm |
| 4 | 10.0% | 3.1 cm | 10 | 3.3%§ | 2.8 cm |
| 5 | 5.2% | 2.4 cm | 11 | 2.2%‡ | 2.5 cm |
| 6 | (one control animal died after surgery) | | 12 | 0.0% | 1.8 cm |
| Average | 11.7% | 2.56 cm | | 3.2% | 2.52 cm |

$P < .01$ for % infarct (t values)
P = probablility of error
t = student ‡ test
*Calculated on the basis of the % of the left ventricular myocardium damaged in a representative section approximately 3mm distal from the tie off point.
+The distance the suture was applied to a branch of the LAD
‡ Sephadex QAE was the carrier for the FGF
§ 25 micrograms of FGF instead of 10 micrograms were utilized

TABLE II

| % of Cat Hearts with Transmural* Infarcts | |
|---|---|
| Control | Treated |
| 80% | 17% |

*Calculated on the basis that at least 2/3 the wall of the myocardium was involved.

EXAMPLE II

In this Example seven mongrel dogs to be treated and eight mongrel dogs acting as a control were randomly selected weighing from 20 to 30 kilograms per dog. The dogs were then anesthetized with barbituates at a level such as to substantially stop breathing. The dogs were then ventilated on a Harvard respirator at 14 to 16 breaths per minute. Heart rate and blood pressure were monitored. The chest of each dog was opened to open the pericardium and suture it to the chest wall exposing the heart and isolating a large coronary artery, i.e., the left anterior descending coronary artery. A catheter was inserted into the left artrium. The left anterior descending coronary artery of each dog was then occluded for five minutes as by clamping. This causes the anterior surface of the heart to become ischemic. The left atrium was then injected with microspheres through the catheter. The microspheres are conventional beads of 10 to 20 micron size labeled with technesium isotope. Injection of the isotope into the left atrium effectively labels all areas of the heart except those tied off by the occluded coronary.

In the next step, the occlusion is released and blood flow restored. FGF carried in a Sephadex suspension as previously described is then injected into the area of risk, which area of risk is defined as that area affected when the coronary artery was tied off. The injection is made with 100 micrograms total FGF in 10 separate injections into the risk tissue. In a next step, 10 minutes after the injection, the same coronary vessel is clamped and occluded for 6 hours. Following this the animals are sacrificed with each heart removed and cut into multiple transverse sections approximately 4 millimeters thick.

Triphenyltetrazolium chloride (TTC) dye is used to strain each slide. Dehydrogenase stains red while the lack of the enzyme stains gray thus enabling one to determine the area of occlusion and dead tissue as opposed to the viable area. The area which has been destroyed by the procedure in each heart is measured as is the total area of the left ventricle of the heart. In the attached Table III, TTC-infarct column indicates the percent of the left ventricle that is destroyed. The column entitled "myocardium at risk" indicates the area as a percentage of the left ventricle which is subject to risk in the test, i.e., the area that is affected by tying off the coronary. While the column entitled "Infarct in percentage of myocardium at risk" is the percentage of infarcted area to possibly infarcted area.

The TTC test can be done by incubating a slice of heart for 10 minutes at 37° C. adjacent a dye-containing paper. The autoradiograph test is done with the microspheres as previously described. The slices of the heart are placed on an X-ray plate and then autoradiated for 18 hours to determine the percentage of the left ventricle affected.

Note that the mean denoted at X for TTC infarct in the control dogs as opposed to the treated dogs varies from 22.5% to 29.4% which is in fact a significant figure. This significance is further attested to by the infarct in % myocardium at risk, where the treated dogs showed 77.9% as opposed 103.5% in untreated dogs. These numbers are significant.

TABLE III

| FGE Treated Dog No. | Date | TTC-Infarct % left ventricle | Myocardium at Risk Autoradiograph % left ventricle | Infarct in % Myocardium at Risk Autoradiograph |
|---|---|---|---|---|
| 1 | 12/20/79 | 19.30 | 34.30 | 56.30 |
| 2 | 1/3/80 | 10.70 | 11.90 | 89.90 |
| 3 | 1/30/80 | 18.30 | 23.80 | 76.90 |
| 4 | 3/17/80 | 22.80 | 32.00 | 71.20 |
| 5 | 3/18/80 | 26.50 | 30.90 | 85.80 |
| 6 | 3/19/80 | 31.30 | 39.00 | 80.30 |
| 7 | 3/20/80 | 28.90 | 29.50 | 98.60 |
| mean $\bar{x}$ | | 22.5 | 28.8 | 77.9 |
| sd | | 7.1 | 8.8 | 13.7 |
| SEM | | | | 5.2 |

| Control Dog No. | Date | TTC-Infarct % left ventricle | Myocardium at Risk Autoradiograph % left ventricle | Infarct in % Myocardium at Risk Autoradiograph |
|---|---|---|---|---|
| 1 | 12/28/79 | 31.50 | 32.00 | 98.40 |
| 2 | 1/17/80 | 27.40 | 21.80 | 123.00 |
| 3 | 1/18/80 | 33.20 | 29.20 | 113.00 |
| 4 | 2/6/80 | 30.00 | 26.80 | 111.00 |
| 5 | 2/7/80 | 30.20 | 30.90 | 97.70 |
| 6 | 2/28/80 | 16.90 | 18.40 | 97.40 |
| 7 | 3/20/80 | 27.70 | 29.40 | 98.20 |
| 8 | 1/25/80 | 38.50 | 35.50 | 88.70 |

TABLE III-continued

| mean $\bar{x}$ | 29.40 | 28.0 | 103.5 |
|---|---|---|---|
| sd | 6.20 | 5.6 | 11.2 |
| SEM | | | 3.97 |
| t | 2.01 | 0.21 | 3.68 |
| p | 0.05 | NS | <0.01 |

While the above examples have been shown and described, many variations are possible. While the mechanism by which FGF acts to maintain viability in areas of the heart subject to ischemic disease is not known, it does maintain viability for a sustained period of time and salvage such areas. The mechanism may be obtaining improved and sustained blood flow over greater areas of the heart than would otherwise happen after myocardial infarction. In many cases of improvement with the FGF treatment, improved blood flow is found in the salvage area and surrounding it. This may occur due to revascularization. The drug can be administered prior to, during or after myocardial infarction. The FGF can be administered prior to or during bypass or open heart surgery to reduce damage to the heart as by death of tissue, during and after such surgical procedures. Direct injection into the tissue or into the coronary heart vessels in the amounts described above is preferably used. The drug seems to be specific to the heart, and can provide sustained flow of blood for hours in heart muscle tissue at areas at and around myocardial infarctions. The dosage level can vary greatly depending upon the individual, the species being treated which can be any mammal and other factors.

The FGF used has a series of proteins in addition to the approximately 13,400 molecular weight FGF. These proteins include those known to be obtained in Sephadex G75 gel filtration or in CM cellulose column chromatography by the Gospodarowicz method. One or any combination of these molecular weight band materials so obtained can be effective to reduce myocardial infarcted areas and are considered with the scope of the present invention and used within the term FGF as used in this specification and claims. The term further includes FGF obtained from other sources such as humans or other mammals.

I claim:

1. A method of treating an area in the heart of a patient subjected to ischemic heart disease, to maintain viability in that area for a sustained time period to salvage said area, said method comprising applying an effective dose of FGF to the heart.

2. A method in accordance with the method of claim 1 wherein said patient is treated in vivo by direct injection of FGF in the heart.

3. A method in accordance with the method of claim 1 wherein said patient is treated by injecting said FGF intravenously.

4. A method in accordance with the method of claim 1 wherein said patient is treated by direct injection of 10 micrograms to 1 gram/100 grams of heart.

5. A method in accordance with the method of claim 2 wherein said patient is treated by direct injection of 10 micrograms to 1 gram/100 grams of heart.

6. A method in accordance with the method of claim 4 wherein said patient is treatd by direct injection of 10 micrograms to 1 gram/100 grams of heart.

7. A method in accordance with the method of claim 2 wherein blood flow in said area is increased over that which would occur in the area without treatment with FGF.

8. A method in accordance with the method of claim 1 wherein said FGF is applied by a method selected from the group consisting essentially of oral ingestion, subcutaneous injection, intramuscular injection, myocardial injection and intravenous injection.

9. A method in accordance with the method of claim 4 wherein said injection is of FGF carried in a slow release material.

10. A method in accordance with the method of claim 5 wherein said injection is of FGF carried in a. slow release material.

11. A method in accordance with the method of claim 6 wherein said injection is of FGF carried in a slow release material.

12. A method in accordance with the method of claim 1 wherein said dose is administered during open heart surgery.

13. A method of treating a coronary patient to affect the heart of the patient, said method comprising applying an effective dose of FGF to the patient so as to treat the heart of the patient.

* * * * *

UNITED STATES PATENT AND TRADEMARK OFFICE
CERTIFICATE OF CORRECTION

PATENT NO. : 4,296,100

DATED : October 20, 1981

INVENTOR(S) : Wayne P. Franco

It is certified that error appears in the above—identified patent and that said Letters Patent is hereby corrected as shown below:

Column 2, line 23, after "-20°", insert --after--.
Column 4, line 61, please cancel "artrium" and insert --atrium--.
Column 5, line 9, after "the" please insert --area of--.
Column 5, line 16, please cancel "strain" and insert --stain--.
Column 5, line 47, please cancel "FGE" and insert --FGF--.
Column 6, line 40, please cancel "with" and insert --within--.

Signed and Sealed this

Fifteenth Day of June 1982

[SEAL]

Attest:

GERALD J. MOSSINGHOFF

Attesting Officer    Commissioner of Patents and Trademarks